US00PP21693P3

(12) United States Plant Patent
Wagner

(10) Patent No.: US PP21,693 P3
(45) Date of Patent: Feb. 1, 2011

(54) ***PENNISETUM ALOPECUROIDES* PLANT NAMED 'PAV300'**

(50) Latin Name: *Pennisetum alopecuroides*
Varietal Denomination: PAV300

(76) Inventor: Tobey Wagner, P.O. Box 460, Mt. Pleasant, SC (US) 29465

( * ) Notice: Subject to any disclaimer, the term of this patent is extended or adjusted under 35 U.S.C. 154(b) by 0 days.

(21) Appl. No.: 12/290,055

(22) Filed: Oct. 28, 2008

(65) Prior Publication Data

US 2009/0126054 P1 May 14, 2009

Related U.S. Application Data

(60) Provisional application No. 61/001,643, filed on Nov. 2, 2007.

(51) Int. Cl.
*A01H 5/00* (2006.01)

(52) U.S. Cl. ..... Plt./384

(58) Field of Classification Search ..... Plt./384
See application file for complete search history.

*Primary Examiner*—Susan B McCormick Ewoldt

(57) ABSTRACT

A new and distinct variety of *Pennisetum alopecuroides* plant named 'PAV300' is characterized by its semi-dwarf and compact, dense growth habit with green-white variegated leaves that are finer and more narrow than other varieties of *Pennisetum alopecuroides*. 'PAV300' is further characterized by a medium-sized inflorescence which is green with a purple tinge.

5 Drawing Sheets

Latin name of the genus and species: The Latin name of the genus and species of the novel variety disclosed herein is *Pennisetum alopecuroides.*

Variety demonination: The inventive variety of *Pennisetum alopecuroides* disclosed herein has been given the variety denomination 'PAV300'.

BACKGROUND OF THE INVENTION

The present invention relates to a new and distinct perennial variety of *Pennisetum alopecuroides,* which has been given the variety denomination of 'PAV300'. Its market class is that of a perennial ornamental grass, intended for use in landscaping as a decorative grass.

The *Pennisetum alopecuroides* variety 'PAV300' was first discovered in a tissue culture laboratory in the year 2005 in the state of Florida, USA as a variegated mutation from the controlled micro propagation of *Pennisetum alopecuroides.* The parent was *Pennisetum alopecuroides* 'PA300' (Australian Plant Breeders Rights Application No. 2001-091 and not patented in the USA). 'PAV300' was selected for its green-white variegated foliage as compared with its parent 'PA300'. 'PAV300' was first propagated asexually by division in 2005 at a greenhouse in Arcadia, Fla., USA and has since been asexually propagated by divisions in the state of South Carolina, USA. The distinctive characteristics of the inventive 'PAV300' variety are stable from generation to generation; clones of the variety produced by asexual reproduction maintain the distinguishing characteristics of the original plant.

'PAV300' has a semi-dwarf and compact growth habit with leaves that are finer and more narrow than those of *Pennisetum alopecuroides* 'PA400' (not patented), *Pennisetum alopecuroides* common form, and *Pennisetum alopecuroides* 'Viridescens' (not patented). It is taller and has a wider leaf than 'Kang-net Dwarf' (not patented). In addition, 'PAV300' has a medium-length seed head.

SUMMARY OF THE INVENTION

'PAV300' is a distinctive variety of *Pennisetum alopecuroides* which is characterized by unique green-white variegated foliage, and a dense, semi-dwarf growth habit.

BOTANICAL DESCRIPTION OF THE PLANT

The following is a detailed botanical description of a new and distinct variety of a *Pennisetum alopecuroides* ornamental grass known as 'PAV300'. The descriptions disclosed herein are based upon observations of the plant grown in nursery pots and field plots in South Carolina, USA. The data presented in Tables 1-4, below, were obtained from mature plants that were approximately ten months old on Oct. 23, 2007 when the trials commenced. Those skilled in the art will appreciate that certain characteristics will vary with older or, conversely younger plants. 'PAV300' has not been observed under all possible environmental conditions. All colors cited herein refer to The Royal Horticultural Society Colour Chart designations except where general terms of ordinary dictionary significance are used. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like.

'PAV300' is a perennial *Pennisetum alopecuroides* which is the result of a genetic mutation of the maternal parent 'PA300' (Australian Plant Breeders' Rights Application No. 2001/091). After its selection, 'PAV300' was asexually propagated by division. 'PAV300' is a green-white variegated plant, which is unusual for *Pennisetum alopecuroides* plants of similar size, as these plants usually have a monochromatic green leaf blade color.

Growth Habit, Dimensions and Color

'PAV300' is a compact, semi-dwarf, clump forming plant with an average height of 45 cm and an average width of 45 cm. The leaf has an average width of 4.7 mm, which is unusual for this species given the height of this variety, and reaches an average length of 719 mm. The average number of divisions of the basal shoot, per 1 gallon (trade) pot, is 48.5. The leaf is generally uniform in width from the base to ⅔ from the tip and has a point tip, typical of *Pennisetum alopecuroides*. The leaf color of 'PAV300', upper and lower leaf, is variegated green and white: green 138A and white 156C. The inflorescence (flower spike) is green with a purple tinge and has an average length of 141 mm. Furthermore, 'PAV300' appears to flower later than other *Pennisetum alopecuroides* varieties. These features and other characteristics are apparent from the Tables provided herein.

Inflorescence

Figure 3:
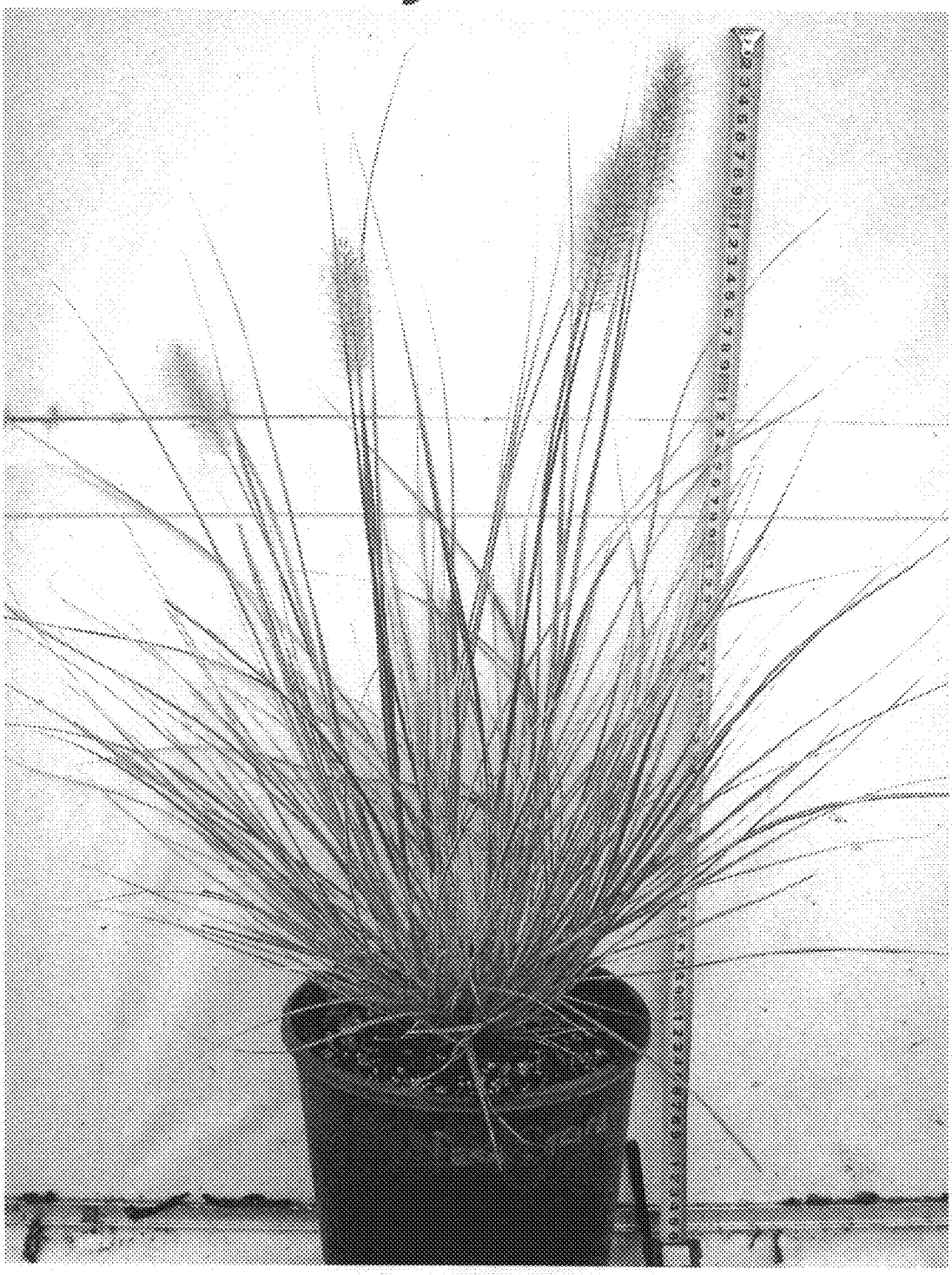
FIG. 3 shows 'PAV300' flowering habit: inflorescence attitude, spread and height.
Figure 4:
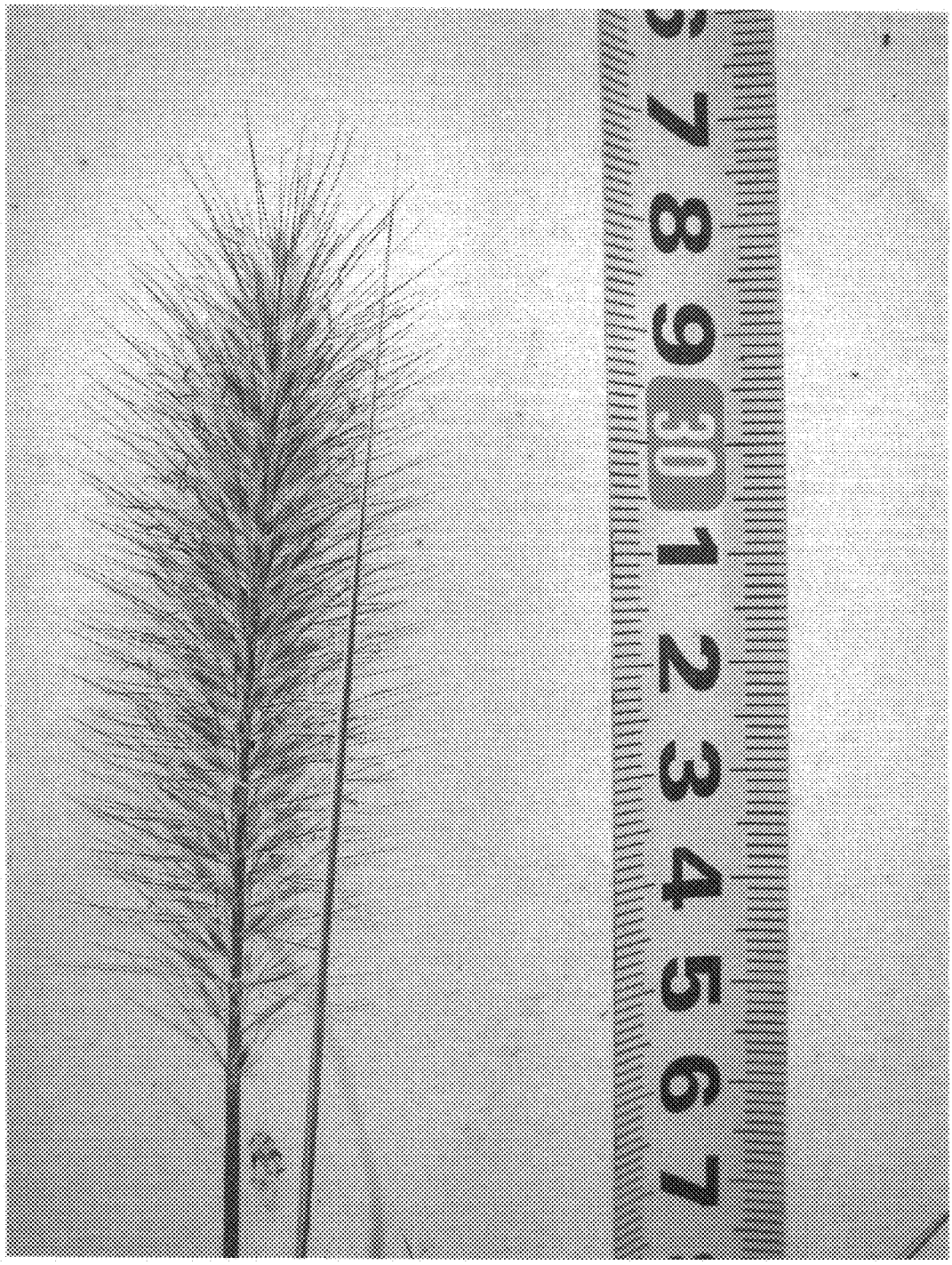
FIG. 4 show 'PAV300' spike detail
Figure 5:
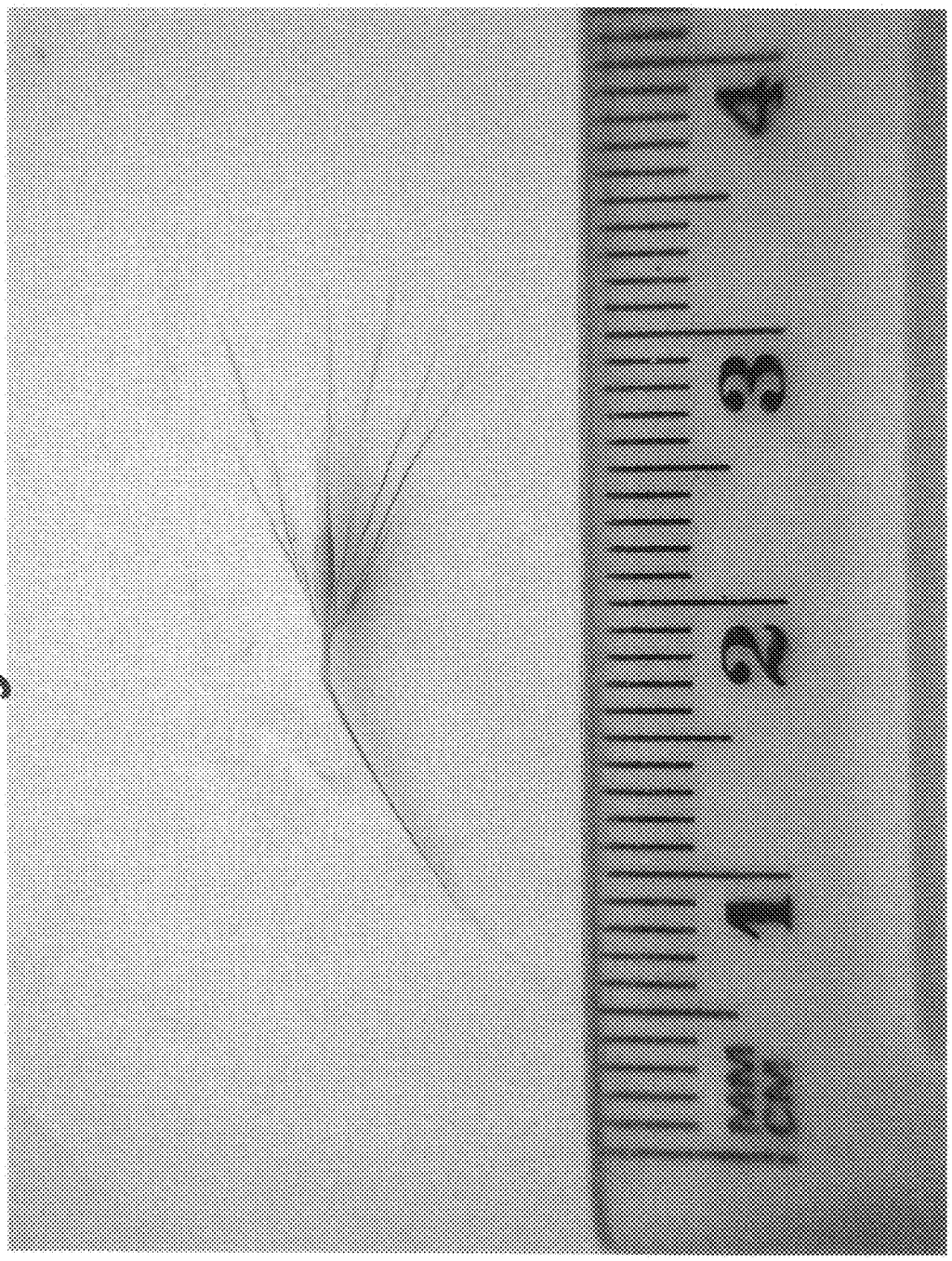
FIG. 5 show 'PAV300' spikelet detail including bristles.

The inflorescence is a spike-like panicle borne on a stem of average length 719 mm and color yellow green RHS146A (see FIG. 3). There is an average of 6 panicles per plant. The average spike length is 141 mm (see FIG. 4). and the average spike with including bristles is 35 mm. There are up to 135 spikelets per spike and each is of length range 7–9 mm not including the bristles or 16–20 mm including the bristles (see FIG. 5). Each spikelet is borne on a stalk 1–2 mm long and of color yellow green RHS 144A. The glumes are also variegated, typically by a longitudinal stripe of contrasting yellow green RHS 144A and orange white approximating to RHS159D. The bristles are colored grayed purple approximating to RHS N186D and there are usually 7–10 resent per spikelet. Bristle length is typically 2–3 times the length of the spikelet. The color of the bristles contributes to the overall purple tinge of the spike.

'PAV300' Compared with Other Varieties of *Pennisetum alopecuroides*

Figure 1:
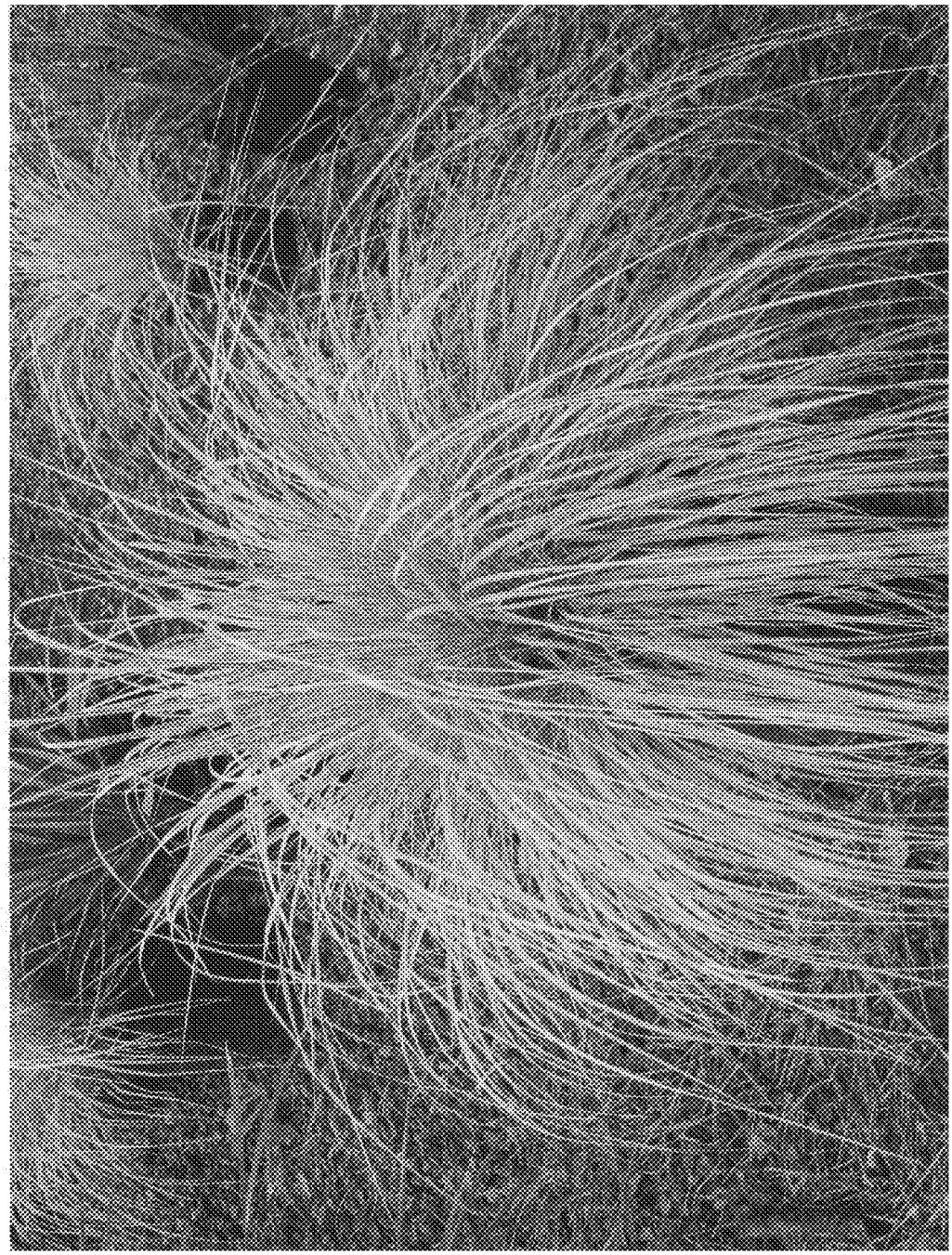
FIG. 1 is 'PAV300' foliage showing growth habit: leaf attitude, spread, variegation pattern and leaf colors.
Figure 2:
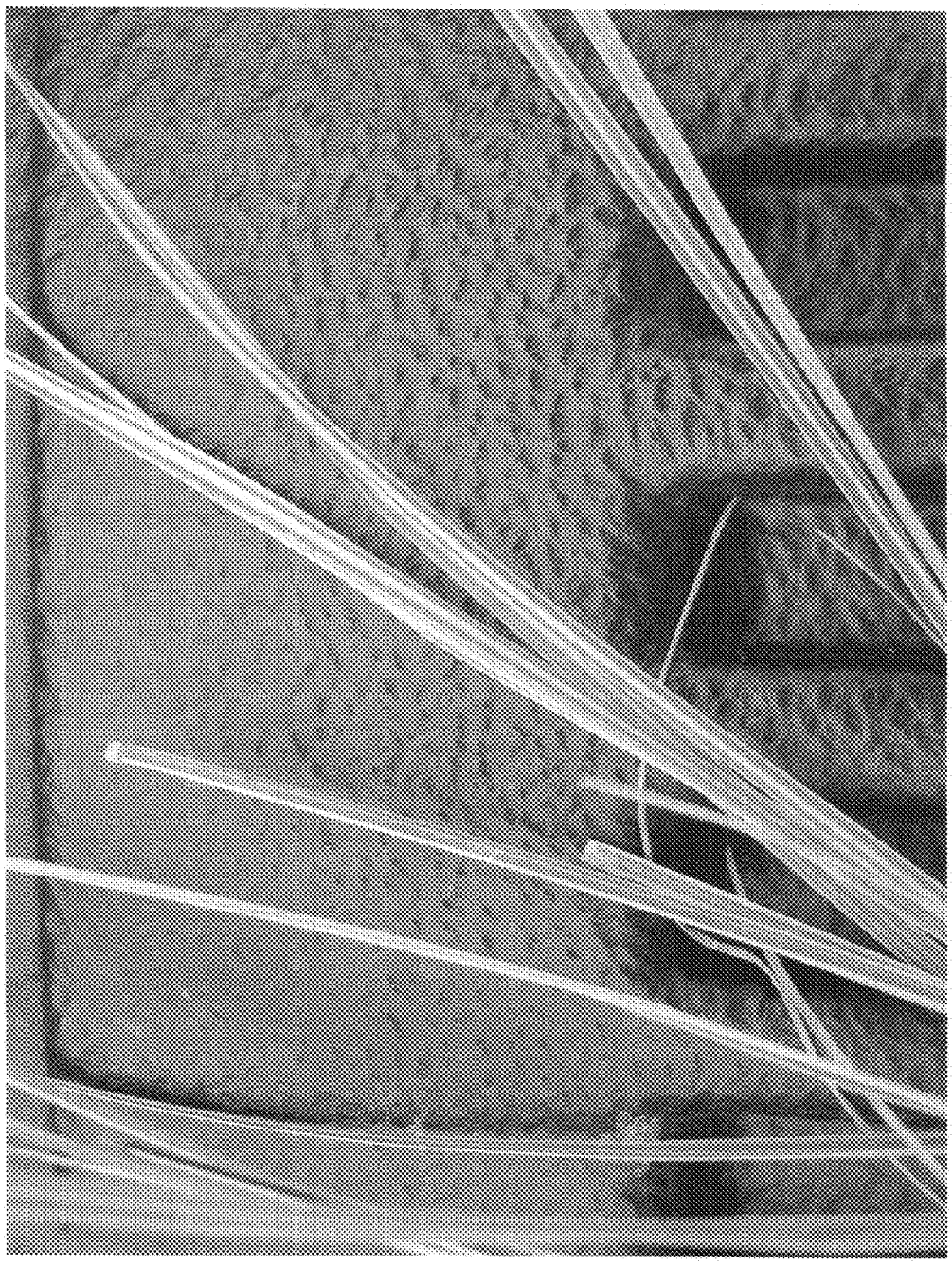
FIG. 2 shows a 'PAV300' leaf sections showing variegation pattern and leaf color.

The leaf color of 'PAV300' is variegated green 138A and white 156C (FIGS. 1 and 2), as compared with PA300 which is 143B; and 'Kang-net Dwarf' and 'PA400', the leaves of which are green 143A.

The novelty and distinctiveness of 'PAV300' as compared with other varieties of *Pennisetum alopecuroides* are further illustrated by vegetative (Table 1) and inflorescence (Table 2) measurements.

TABLE 1

| Variety | Blade Width* (mm) | Basal Shoot Width (mm) | Blade Length from Stem* (mm) | Leaf Height from Base† (mm) |
|---|---|---|---|---|
| 'PAV300' | 4.7 | 8.1 | 448 | 684 |
| 'PA300' | 4.7 | 8.1 | 448 | 684 |
| 'PA400' | 6.2 | 13.2 | 760 | 1331 |
| Common Form | 6.1 | 12.8 | 754 | 1318 |

TABLE 1-continued

| Variety | Blade Width* (mm) | Basal Shoot Width (mm) | Blade Length from Stem* (mm) | Leaf Height from Base† (mm) |
|---|---|---|---|---|
| 'Viridescens' | 8.6 | 12.6 | 370 | 585 |
| 'Kang-net Dwarf' | 3.1 | 7.1 | 253 | 366 |

*Indicated average.
†includes basal shoot.
Test Plots were planted on Apr. 1, 2007 in Awendaw, South Carolina.

TABLE 2

| Variety | Seed Head Color | Flower Spike Length*† (mm) | Flower Spike Length (mm) (Seed Head Only) |
|---|---|---|---|
| 'PAV300' | Light Purple/Green | 719 | 141 |
| 'PA300' | Light Purple/Green | 719 | 141 |
| 'PA400' | Purple | 1324 | 203 |
| Common Form | Variable, Purple, Green, Cream | 1292 | 192 |
| 'Viridescens' | Dark Purple to Black | 591 | 111 |
| 'Kang-net Dwarf' | Green/Brown | 526 | 71 |

*Indicates average.
†Measurements were taken of the whole stem from the base of the plant. Test Plots were planted on Apr. 1, 2007 in Awendaw, South Carolina.

Asexual Reproduction

After its initial discovery, 'PAV300' was transplanted into a 1 gallon pot for further trials and testing. After divisions were made for several subsequent generations, 'PAV300' was observed to retain variegation, size, and fine leaf characteristics that were noted in the original 'PAV300' seedling. 'PAV300' was then divided into many larger pots for further evaluation.

During these divisions, it was noted that 'PAV300' produced 43 to 54 divisions per 1 gallon (trade size) pot. In comparison, 'PA400' produced 12 to 17 divisions, common *Pennisetum alopecuroides* produced 9 to 26 divisions, 'Viridescens' produced 11 to 14 divisions, and 'Kang-net Dwarf' produced 58 to 74 divisions. More extensive data regarding division rates per 1 gallon (trade size) pot and 3 gallon (trade size) pot of 'PAV300' as compared with other *Pennisetum alopecuroides* are presented in Table 3.

TABLE 3

| Variety | Divisions per 1 gallon (trade size) Pot (Range) | Divisions per 3 gallon (trade size) Pot (Range) |
|---|---|---|
| 'PAV300' | 43 to 54 | 78 to 87 |
| 'PA300' | 43 to 54 | 78 to 87 |
| 'PA400' | 12 to 17 | 31 to 39 |
| Common Form | 9 to 26 | 22 to 48 |
| 'Kang-net Dwarf' | 58 to 74 | 101 to 127 |
| 'Viridescens' | 11 to 14 | 22 to 28 |

Test Plots were planted on Apr. 1, 2007 in Awendaw, South Carolina. Divided Jun. 15, 2007 from pots other than those used in Tables 1 and 2.

Divisions of 'PAV300' root within 2 weeks, which is faster than the 3 to 4 weeks typical of *Pennisetum alopecuroides* common and 'PA400'. The survival rate of 'PAV300' division is 94%, while the survival rate of *Pennisetum alopecuroides* common is approximately 63% and 'PA400' is approximately 61%. A more detailed comparison of division survival rate is listed in Table 4.

TABLE 4

| Variety | No. of Divisions that Survived Out of 200 |
|---|---|
| 'PAV300' | 188 |
| 'PA300' | 188 |
| 'PA400' | 121 |
| Common Form | 126 |
| 'Kang-net Dwarf' | 196 |
| 'Viridescens' | 178 |

Test Plots were located in Awendaw, South Carolina.

Divided Jun. 15, 2007 from pots other than those used in Tables 1 and 2. Potting mix used contained 50% perlite and 50% peat. Plants were divided into 72-cell propagation trays.

Environmental Tolerances

'PAV300' has shown some potential for shade tolerance and further shade tolerance tests are underway. The winter hardiness of 'PAV300' is at least to zone 8b, and evaluation of winter hardiness is ongoing.

That which is claimed is:

1. A new and distinct variety of *Pennisetum alopecuroides* plant named 'PAV300', substantially as described and illustrated herein.

* * * * *